United States Patent
Watanabe et al.

[11] Patent Number: 5,856,259
[45] Date of Patent: Jan. 5, 1999

[54] PREPARATION PROCESS OF SUPPORTED CATALYST FOR THE SYNTHESIS OF METHACROLEIN AND METHACRYLIC ACID

[75] Inventors: Seigo Watanabe; Hitoshi Yoshioka; Jinko Izumi, all of Otake, Japan

[73] Assignee: Mitsubishi Rayon Co., Ltd., Tokyo, Japan

[21] Appl. No.: 849,531

[22] PCT Filed: Dec. 15, 1995

[86] PCT No.: PCT/JP95/02577

§ 371 Date: Jun. 20, 1997

§ 102(e) Date: Jun. 20, 1997

[87] PCT Pub. No.: WO96/19290

PCT Pub. Date: Jun. 27, 1996

[30] Foreign Application Priority Data

Dec. 21, 1994 [JP] Japan ................................. 6-335117

[51] Int. Cl.[6] ....................................... B01J 23/00
[52] U.S. Cl. ........................... 502/305; 502/311
[58] Field of Search .................... 502/311, 205, 502/212, 215, 255, 306, 307, 308, 309, 211, 209, 220; 562/532

[56] References Cited

FOREIGN PATENT DOCUMENTS

| | | |
|---|---|---|
| 55-127328 | 10/1980 | Japan . |
| 56-2926 | 1/1981 | Japan . |
| 59-31727 | 2/1984 | Japan . |
| 63-2946 | 1/1988 | Japan . |
| 63-315147 | 12/1988 | Japan . |
| 2-25443 | 1/1990 | Japan . |
| 5-286886 | 11/1993 | Japan . |

*Primary Examiner*—Gary P. Straub
*Assistant Examiner*—Tanaga A. Boozer
*Attorney, Agent, or Firm*—Armstrong, Westerman, Hattori, McLeland & Naughton

[57] ABSTRACT

A process for producing a supported catalyst for the synthesis of methacrolein and methacrylic acid in which a catalytic active substance comprising a composite oxide containing molybdenum and bismuth as essential components is supported on the inside surface and/or the outside surface of an inert carrier, which comprises the steps of drying a mixed solution or an aqueous slurry containing the compounds of the elements constituting the catalytic active substance, subjecting the dried product to a primary calcination at a temperature in a range of 200°–400° C. to form a catalytic active substance precursor, comminuting the obtained catalytic active substance precursor to such an extent that the medium particle size in the volume-based particle size distribution becomes 10 $\mu$m or less, supporting the comminution product on an inert carrier, and subjecting it to a secondary calcination at a temperature which is 100° C. or more higher than the primary calcination temperature.

4 Claims, No Drawings

PREPARATION PROCESS OF SUPPORTED CATALYST FOR THE SYNTHESIS OF METHACROLEIN AND METHACRYLIC ACID

TECHNICAL FIELD

The present invention relates to a process for the preparation of a supported catalyst used for the synthesis of methacrolein and methacrylic acid through gas phase catalytic oxidation of isobutylene or tertiary butanol with molecular oxygen.

BACKGROUND ART

Many proposals have been made (JP-A-55-127328, JP-A-56-2926, U.S. Pat. No. 435,404, U.S. Pat. No. 4,446,328, JP-A-59-31727, etc.) regarding the catalysts used in the preparation of methacrolein and methacrylic acid through catalytic oxidation of isobutylene or tertiary butanol in a high-temperature gaseous phase. These proposals, however, mostly concern the catalyst components and their ratios. Few of these proposals make mention of preparation process of supported catalyst, and none of them refers to particulars of the catalytic active substance to be supported, such as particle size thereof and calcination conditions for the production of such substance.

In the production of a catalyst used for the preparation of methacrolein and methacrylic acid through gas phase catalytic oxidation of isobutylene or tertiary butanol with molecular oxygen in a fixed bed reactor, since this reaction is exothermic type, it is desirable to bulk up the catalytic active substance while controlling the thickness of the catalyst layer to avoid the undesirable rise of temperature due to build-up of heat in the catalyst layer. Control of the thickness of the catalyst layer is also desirable for inhibiting the consecutive reactions of the product. Therefore, use of a supported catalyst having a catalytic active substance supported on a carrier and the controlled thickness of the catalyst layer often prove to be favorable for the selectivity of the objective product.

JP-A-2-25443 discloses a production process of a supported catalyst used for the preparation of acrolein, according to which a catalytic active substance precursor ground to a particle size of about 400 μm is supported on an inert carrier. JP-A-58-930 discloses a production process of a supported catalyst used for the preparation of acrolein or methacrolein, and in an embodiment thereof, there is shown a method for supporting a catalytic active substance precursor ground to a particle size distribution of around 2–80 μm, with the mode of the particles falling in a range of about 10–30 μm, on an inert carrier. According to this method, the primary calcination for obtaining a catalytic active substance precursor is carried out at around 500° C., and the secondary calcination conducted after the supporting operation is carried out at a temperature which is approximately 20° C. higher than the primary calcination temperature. The supported catalysts obtained from these methods are still unsatisfactory for industrial use in such respects as catalytic activity, selectivity of the objective product and mechanical strength, and further improvements have been desired from the industrial standpoint.

DISCLOSURE OF INVENTION

The present invention has an object to provide a novel production process of a catalyst for the synthesis of methacrolein and methacrylic acid, specifically a supported catalyst used for the synthesis of methacrolein and methacrylic acid through gas phase catalytic oxidation of isobutylene or tertiary butanol with molecular oxygen.

According to the present invention, there is provided a process for producing a supported catalyst for the synthesis of methacrolein and methacrylic acid, said supported catalyst having a catalytic active substance incorporated on the inside surface and/or the outside surface of an inert carrier, said catalytic active substance comprising a composite oxide containing molybdenum and bismuth as essential components, which process comprises the steps of drying a mixed solution or an aqueous slurry of the compounds of the elements constituting said catalytic active substance, subjecting the dried product to a primary calcination at a temperature falling in a range of 200°–400° C. to form a catalytic active substance precursor, comminuting the thus obtained precursor to such an extent point that the medium particle size in the volume-based particle size distribution becomes 10 μm or less, preferably 5 μm or less, supporting the obtained comminution product on an inert carrier, and subjecting it to a secondary calcination at a temperature which is 100° C. or more higher than the primary calcination temperature.

Best Mode for Carrying Out the Invention

The catalytic active substance supported on the inside surface and/or the outside surface of an inert carrier preferably comprises a composite oxide represented by the following formula:

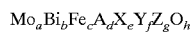

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, germanium, cerium, niobium, titanium, zirconium, tungsten and antimony; Z represents at least one element selected from the group consisting of potassium, sodium, rubidium, cesium and thallium; and a, b, c, d, e, f, g and h represent the ratios of atoms of the respective elements, wherein when a=12, $0.1 \leq b \leq 5$, $0.1 \leq c \leq 5$, $1 \leq d \leq 12$, $0 \leq e \leq 10$, $0 \leq f \leq 10$ and $0.01 \leq g \leq 3$, and h is the number of the oxygen atoms necessary for satisfying the valences of the respective elements.

In the present invention, the starting materials of the elements constituting the catalytic active substance are not specified, but usually the oxides or the chlorides, hydroxides, sulfates, nitrates, carbonates, ammonium salts or mixtures thereof which can be made into oxides by strong heating are employed.

The type of the inert carrier used in the present invention is also not specified; ordinary carrier materials such silica, alumina, silica-alumina, magnesia, titania and the like can be used. The shape of the carrier is not defined; it may, for instance, be spherical, columnar, ring-like or plate-like.

In the present invention, various types of commonly used driers such as box drier, spray drier, drum drier, slurry drier, etc., can be employed for drying the mixed solution or aqueous slurry containing the compounds of the elements constituting the catalytic active substance. The term "drying" used in the present invention means that water is removed from said mixed solution or aqueous slurry to such an extent that a substantially solid residue (hereinafter referred to as dried product) can be obtained. The water content of the dried product is not specified. The shape of the dried product is also not specified; it may, for instance, be powdery or block-like.

The primary calcination in the present invention is a step in which the dried product containing the catalyst components is heat treated to form a precursor structure of the catalytic active substance. This primary calcination is carried out in a temperature range of 200°–400° C., preferably 230°–360° C. In case a nitrate or an ammonium salt is used as starting catalytic material, it is desirable to remove the nitrate group or ammonium group to a certain extent during the primary calcination, and for this purpose, the calcination is preferably carried out at a temperature above 200° C.

The active site of the catalyst produced according to the present invention is usually generated when the catalyst precursor containing the catalyst components is calcined (heat treated) at 450°–600° C. In the present invention, the active site of the catalyst is kept from coming out in the stage of the primary calcination. Therefore, the primary calcination is carried out at a temperature below 400° C., preferably below 360° C. The calcination time is not specified, but it is preferably in a range of 10 minutes to 5 hours.

The catalytic active substance precursor obtained from the primary calcination is then comminuted. It is important that the precursor be comminuted to such an extent that the medium particle size in their volume-based particle size distribution will become 10 μm or less, preferably 5 μm or less. The method of comminution is not specified, but wet comminution using an ordinary homogenizer, attritor or the like is preferred because of simple operation, easy control of particle size and other factors. It is more desirable to carry out wet comminution of 100 parts by weight of the catalytic active substance precursor in a state of being dispersed in or wetted with 50–200 parts by weight of a liquid substance, preferably water.

The "medium particle size in the volume-based particle size distribution" in the present invention designates the particle diameter Dp when the volume of the particles having a diameter of Dp or greater holds just 50% of the total volume of the whole particles. In the case of the present invention, since the true specific gravity of each of the catalytic active substance precursor particles after the comminution is considered constant regardless of the particle size, the volume-based particle size distribution may be regarded as synonymous with the mass-based particle size distribution.

The present inventors found that by subjecting the catalytic active substance precursor to the above comminution treatment, the finally obtained supported catalyst is improved in catalytic activity, selectivity of the objective product and mechanical strength. It was further found that the improvement of catalytic activity and selectivity of the objective product in the present invention is attributable not only to the increase of specific surface area of the catalytic active substance by comminution thereof but also to the acceleration of the catalytic active site generating reaction which is induced by the secondary calcination described below due to the increase of contact area between the particles.

The comminuted catalytic active substance precursor is supported on an inert carrier and then subjected to the secondary calcination at a temperature which is 100° C. or more higher than the primary calcination temperature.

The ordinary methods such as impregnation method, immersion method, etc., can be used for supporting the comminuted catalytic active substance precursor on an inert carrier.

In case the precursor is comminuted by the wet comminution as described above, it is recommended to employ a supporting method in which the obtained wet comminuted material, or a slurry thereof formed by adding an appropriate amount of a liquid substance to said comminuted material, is deposited on an inert carrier while evaporating away the liquid substance simultaneously. The liquid substance used here is not specified; a substance which is easily evaporated on heating and harmless to the catalyst, such as water, alcohols, ketones, esters, etc., can be used. Water is recommended for industrial practice of the process.

In the comminuted material may be contained appropriate additives, for example, inorganic salts such as barium sulfate, ammonium nitrate, etc., organic materials such as celluloses, starch, polyvinyl alcohol, stearic acid, etc., hydroxide sols such as silica sol, alumina sol, etc., and inorganic fibers such as whisker, glass fiber, carbon fiber, etc., for the purpose of controlling specific surface area, pore volume and pore distribution of the catalytic active substance layer with good reproducibility or for enhancing mechanical strength of said catalytic substance. Of these additives, glass fiber is preferably used.

The "secondary calcination" in the present invention is a step in which the catalytic active substance precursor supported on an inert carrier is calcined (heat treated) to develop the active site of the catalyst. This secondary calcination is carried out at a temperature which is 100° C. or more higher than the primary calcination temperature, preferably in a range of 450°–600° C., more preferably 480°–550° C.

The reaction that occurs in the secondary calcination step for developing the active site of the catalyst is a solid phase reaction. This solid phase reaction proceeds in the inside of and at the contact areas between the particles of catalytic active substance precursor supported on an inert carrier. Therefore, if the contact areas between said precursor particles are enlarged by comminuting the precursor as finely as possible before supporting it on an inert carrier, the solid phase reaction is promoted.

The secondary calcination time is not specified, but it is recommended to continue this treatment for at least one hour since the solid phase reaction does not proceed sufficiently if the calcination time is too short.

On completion of said secondary calcination, the objective supported catalyst of the present invention is obtained.

In production of methacrolein or methacrylic acid through gas phase catalytic oxidation of isobutylene or tertiary butanol with molecular oxygen by using the supported catalyst obtained according to the present invention, the molar ratio of isobutylene or tertiary butanol to oxygen is preferably 1:0.5~1:3. Isobutylene or tertiary butanol used as starting material is preferably diluted with an inert gas. The molecular oxygen used for oxidation may be pure oxygen gas, but air is preferably used for the industrial applications. The reaction pressure may range from normal pressure to several atmosphere. The reaction temperature is preferably in a range of 300°–450° C.

The present invention is further illustrated by the following Examples. In the Examples, all "parts" are by weight. The particle size distribution was determined by a laser diffraction type particle size distribution meter, and the reaction test analysis was made by gas chromatography. The rate of reaction of the reaction material isobutylene or tertiary butanol and the selectivity of the produced methacrolein and methacrylic acid are defined as follows:

Rate of reaction of reaction material (%) =

$$\frac{\text{Number of moles of the reacted reaction material}}{\text{Number of moles of the supplied reaction material}} \times 100$$

Selectivity of methacrolein (%) =

$$\frac{\text{Number of moles of the produced methacrolein}}{\text{Number of moles of the reacted reaction material}} \times 100$$

Selectivity of methacrylic acid (%) =

$$\frac{\text{Number of moles of the produced methacrylic acid}}{\text{Number of moles of the reacted reaction material}} \times 100$$

The rate of powdering after packing of the supported catalyst is defined as follows: One thousand grams of the supported catalyst is packed in a 2.75 cm$\phi$ and 6 m long stainless steel-made cylindrical container set vertically to the horizontal by dropping the catalyst into the container from the top opening thereof, and then the supported catalyst is recovered from the bottom of the container. Of the recovered supported catalyst, the portion which can not be passed through a 14-mesh screen is represented by Xg.

$$\text{Rate of powdering after packing (\%)} = \frac{1,000 - X}{1,000} \times 100$$

EXAMPLE 1

(Present Invention)

Three thousand parts of ammonium paramolybdate, 185.5 parts of antimony trioxide, 11.3 parts of titanium dioxide and 4.5 parts of tellurium dioxide were added to 6,000 parts of water and heated with stirring to prepare a solution A. Separately from this operation, 150 parts of a 60% aqueous solution of nitric acid, 686.9 parts of bismuth nitrate, 1,144.1 parts of ferric nitrate, 411.7 parts of nickel nitrate, 2,883.9 parts of cobalt nitrate, 363.1 parts of magnesium nitrate and 110.4 parts of cesium nitrate were added successively to and dissolved in 5,500 parts of water to prepare a solution B. The solution B was added to the solution A to form a slurry and then heated with stirring to evaporate away the most part of water.

The resulting cake was dried at 100° C. for 15 hours to obtain a block-like dry product. This dry product was subjected to primary calcination at 300° C. for 3 hours to obtain a catalytic active substance precursor. The thus obtained catalytic active substance precursor had a composition represented by the following composition:

$$Mo_{12}Bi_1Fe_2Ni_1Co_7Mg_1Sb_{0.9}Ti_{0.1}Te_{0.02}Cs_{0.4}O_x$$

wherein Mo, Bi, Fe, Ni, Co, Mg, Sb, Ti, Te, Cs and O represent molybdenum, bismuth, iron, nickel, cobalt, magnesium, antimony, titanium, tellurium, cesium and oxygen, respectively; the numbers affixed to the respective symbols indicate the ratios of atoms of the respective elements; and x is the number of the oxygen atoms necessary for satisfying the valences of the respective elements.

Four hundred parts of the thus obtained catalytic active substance precursor was ground to a size of 24 mesh or less, dispersed in 500 parts of water and then wet comminuted for 30 minutes by a homogenizer. Examining the volume-based particle size distribution of the comminuted catalytic active substance precursor, it was found that the medium particle size was 2.1 $\mu$m. Then 30 parts of glass fibers having an average diameter of 10 $\mu$m and a length of 100–300 $\mu$m were added to the wet comminuted product to prepare a homogeneous slurry (slurry C-1).

Five hundred parts of 4.5 mm-diameter spherical granules of an alumina carrier were introduced into the rotating drum and the slurry C-1 was sprinkled over the carrier gradually while simultaneously heating them by a gas burner from the outside of the drum to evaporate away water. The resulting product was subjected to secondary calcination at 510° C. for 2 hours to obtain a supported catalyst.

The thus obtained supported catalyst was packed in a stainless steel reaction tube and a starting gaseous mixture of 5% of isobutylene, 12% of oxygen, 10% of water vapor and 73% of nitrogen was passed through the catalyst layer for a contact time of 4.5 seconds and reacted at 350° C. The reaction gave the following results: the rate of reaction of isobutylene=96.2%; selectivity of methacrolein=88.1%; selectivity of methacrylic acid=5.3%; the rate of powdering after packing=0.2%, as shown in Table 1.

EXAMPLE 2

(Present Invention)

The procedure of Example 1 was carried out except for use of an attritor in place of the homogenizer for wet comminution. Examination of the particle size distribution of the wet comminuted catalytic active substance precursor showed that this precursor had a medium particle size of 7.2 $\mu$m. Then glass fibers were added to said comminuted precursor in the same was as in Example 1 to form a slurry C-2. By using this slurry, a supported catalyst was prepared in the same way as in Example 1, followed by the same reaction procedure as in Example 1. The results are shown in Table 1. The catalytic performance of the obtained supported catalyst was substantially equal to that of the catalyst obtained in Example 1.

EXAMPLE 3

(Present Invention)

The procedure of Example 1 was followed except that the primary calcination temperature was changed to 230° C. to obtain a slurry C-3. Using this slurry, a supported catalyst was prepared in the same way as in Example 1, followed by the same reaction process as in Example 1. The results are shown in Table 1. The obtained supported catalyst showed the same performance as the catalyst obtained in Example 1.

EXAMPLE 4

(Present Invention)

The procedure of Example 1 was followed except that the primary calcination was carried out at 360° C. to obtain a slurry C-4. Using this slurry C-4, a supported catalyst was prepared in the same way as in Example 1, followed by the same reaction process as conducted in Example 1. The results are shown in Table 1. The obtained carried catalyst showed the same performance as the catalyst obtained in Example 1.

EXAMPLE 5

(Comparative)

Four hundred parts of a catalytic active substance precursor obtained in the same way as Example 1 was dry ground by a drag mill. Examining the volume-based particle size distribution of the ground precursor, it was found that the medium particle size was 30.3 μm. Then 30 parts of glass fibers having an average diameter of 10 μm and a length of 100–300 μm were added to the ground product and the mixture was dispersed in 500 parts of water to form a homogeneous slurry (slurry C-5).

Using this slurry C-5, a supported catalyst was prepared in the same way as in Example 1, followed by the same reaction process as in Example 1. The results are shown in Table 1. The obtained supported catalyst was inferior in performance to the catalyst of Example 1 in many respects such as catalytic activity, selectivity of the objective product and mechanical strength.

EXAMPLE 6

(Comparative)

The procedure of Example 1 was followed except the primary calcination was carried out at 450° C. to obtain a slurry C-6. Using this slurry, a supported catalyst was prepared in accordance with Example 1, followed by the same reaction process as conducted in Example 1. The results are shown in Table 1. The performance of the obtained supported catalyst was inferior in many respects to that of the catalyst obtained in Example 1.

EXAMPLE 7

(Present Invention)

Three thousand parts, of ammonium paramolybdate, 85.1 parts of silicon dioxide and 184.8 parts of ammonium paratungstate were added to 6,000 parts of water and heated with stirring to prepare a solution D. Separately from the above operation, 150 parts of a 60% aqueous nitric acid solution, 824.2 parts of bismuth nitrate, 1,258.5 parts of ferric nitrate, 1,646.7 parts of nickel nitrate, 824.0 parts of cobalt nitrate, 631.8 parts of zinc nitrate, 123.0 parts of cerium nitrate, 41.8 parts of rubidium nitrate and 28.6 parts of potassium nitrate were added successively to 5,500 parts of water and heated with stirring to prepare a solution E. The solution E was added to the solution D to form a slurry and heated with stirring to evaporate away the most part of water.

The resulting cake was dried at 100° C. for 15 hours to obtain a block-like dry product. This dry product was subjected to primary calcination at 270° C. for 3 hours to obtain a catalytic active substance precursor of the following composition:

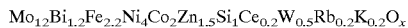

$$Mo_{12}Bi_{1.2}Fe_{2.2}Ni_4Co_2Zn_{1.5}Si_1Ce_{0.2}W_{0.5}Rb_{0.2}K_{0.2}O_x$$

wherein Mo, Bi, Fe, Ni, Co, Zn, Si, Ce, W, Rb, K and O represent molybdenum, bismuth, iron, nickel, cobalt, zinc, silicon, cerium, tungsten, rubidium, potassium and oxygen, respectively; the numbers affixed to the respective elemental symbols indicate the ratios of atoms of the respective elements; and x is the number of the oxygen atoms necessary for satisfying the valences of the respective elements.

Four hundred parts of the thus obtained catalytic active substance precursor was ground to a size of 24 meshes or less, dispersed in 500 parts of water and wet comminuted for 30 minutes by a homogenizer. Examining the volume-based particle size distribution of the comminuted catalystic active substance precursor, it was found that the medium particle size was 1.8 μm. Then 30 parts of glass fibers having an average diameter of 10 μm and a length of 100–300 μm were added to the obtained wet comminuted product to prepare a homogeneous slurry (slurry F-1).

Four hundred parts of 4.5 mm-diameter spherical alumina carrier granules were introduced into a rotating drum, and the slurry F-1 was sprinkled over the carrier gradually while heating it by a gas burner from the outside of the drum to evaporate away water. The obtained supported product was subjected to secondary calcination at 495° C. for 2 hours to obtain a supported catalyst.

Using the thus obtained supported carrier, the same reaction process as in Example 1 was carried out. The results are shown in Table 1. The catalyst performance was good as in Example 1.

EXAMPLE 8

(Comparative)

The procedure of Example 7 was followed except that the primary calcination temperature was changed to 470° C. to obtain a slurry F-2. Then a supported catalyst was prepared in the same way as in Example 7 and subjected to the same reaction process as in Example 7. The results are shown in Table 1. The performance of the obtained supported catalyst was inferior to that of the catalyst of Example 7 in many respects such as catalytic activity, selectivity of the objective product and mechanical strength.

EXAMPLE 9

(Present Invention)

Three thousand parts of ammonium paramolybdate and 8.7 parts of zirconium dioxide were added to 6,000 parts of water and heated with stirring to prepare a solution G. Separately from the above operation, 150 parts of a 60% aqueous nitric acid solution, 32.6 parts of an 85% aqueous phosphoric acid solution, 618.2 parts of bismuth nitrate, 1,430.2 parts of ferric nitrate, 3,295.8 parts of cobalt nitrate, 81.3 parts of manganese nitrate, 46.9 parts of lead nitrate, 110.4 parts of cesium nitrate and 9.6 parts of sodium nitrate were added successively to 5,500 parts of water and heated with stirring to prepare a solution H. The solution H was added to the solution G to form a slurry and heated with stirring to evaporate away the most part of water.

The resulting cake was dried at 100° C. for 15 hours to obtain a block-like dry product. The obtained dry product was subjected to primary calcination at 320° C. for 3 hours to obtain a catalytic active substance precursor. The composition of the obtained catalytic active substance precursor is represented by the following formula:

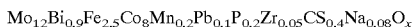

$$Mo_{12}Bi_{0.9}Fe_{2.5}Co_8Mn_{0.2}Pb_{0.1}P_{0.2}Zr_{0.05}CS_{0.4}Na_{0.08}O_x$$

wherein Mo, Bi, Fe, Co, Mn, Pb, P, Zr, Cs, Na and O represent molybdenum, bismuth, iron, cobalt, manganese, lead, phosphorus, zirconium, cesium, sodium and oxygen, respectively; the figures affixed to the respective elemental symbols are ratios of atoms of the respective elements; and x is the number of the oxygen atoms necessary for satisfying the valences of the respective elements.

Four hundred parts of the obtained catalytic active substance precursor were ground to a size of 24 meshes or less, dispersed in 500 parts of water and then wet comminuted for 30 minutes using a homogenizer. Examining the volume-based particle size distribution of the catalytic active substance precursor particles produced by wet comminution, it was found that the medium particle size was 0.9 μm. Then 30 parts of glass fibers having an average diameter of 10 μm and a length of 100–300 μm were added to the obtained wet comminuted product to prepare a homogeneous slurry (slurry I-1).

Into a rotating drum 285.7 parts of 4.5 mm-diameter spherical alumina carrier granules were introduced and the slurry I-1 was sprinkled over the carrier gradually while simultaneously heating it by a gas burner from the outside of the drum to evaporate away water. The resulting supported product was subjected to secondary calcination at 520° C. for 2 hours to obtain a supported catalyst.

Using the thus obtained supported catalyst, the same reaction process as conducted in Example 1 was carried out. The results are shown in Table 1. The catalyst showed good performance as in Example 1.

EXAMPLE 10

(Comparative)

The procedure of Example 9 was followed except that the primary calcination temperature was changed to 520° C. to obtain a slurry I-2. Using this slurry I-2, a supported catalyst was prepared in the same way as in Example 9 and subjected to the same reaction process as in Example 9. The results are shown in Table 1. The obtained supported catalyst was inferior in performance to that of Example 9 in many respects such as catalytic activity, selectivity of the objective product and mechanical strength.

EXAMPLE 11

(Present Invention)

Three thousand parts of ammonium paramolybdate, 38.1 parts of tin oxide and 13.3 parts of germanium dioxide were added to 6,000 parts of water and heated with stirring to prepare a solution J. Separately from the above operation, 150 parts of a 60% aqueous nitric acid solution, 8.8 parts of boric acid, 1.4 parts of concentrated sulfuric acid, 686.9 parts of bismuth nitrate, 1,201 parts of ferric nitrate, 1,235.0 parts of nickel nitrate, 1,235.9 parts of cobalt nitrate, 421.2 parts of zinc nitrate, 37.7 parts of thallium nitrate and 110.4 parts of cesium nitrate were added successively to 5,500 parts of water and heated with stirring to prepare a solution K. The solution K was added to the solution J to form a slurry and heated with stirring to evaporate away the most part of water.

The resulting cake was dried at 100° C. for 15 hours to obtain a block-like dry product. The obtained dry product was subjected to primary calcination at 300° C. for 3 hours to obtain a catalytic active substance precursor. The thus obtained catalytic active substance precursor had a composition represented by the following formula:

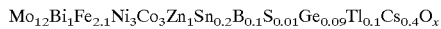

$Mo_{12}Bi_1Fe_{2.1}Ni_3Co_3Zn_1Sn_{0.2}B_{0.1}S_{0.01}Ge_{0.09}Tl_{0.1}Cs_{0.4}O_x$ wherein Mo, Bi, Fe, Ni, Co, Zn, Sn, B, S, Ge, Tl, Cs and O represent molybdenum, bismuth, iron, nickel, cobalt, zinc, tin, boron, sulfur, germanium, thallium, cesium and oxygen, respectively; the figures affixed to the respective elemental symbols are ratios of atoms of the respective elements; and x is the number of the oxygen atoms necessary for satisfying the valences of the respective elements.

Four hundreds parts of the obtained catalytic active substance precursor was ground to a size of 24 meshes or less, dispersed in 500 parts of water and then wet comminuted for 30 minutes by using a homogenizer. Examining the volume-based particle size distribution of the catalytic active substance precursor particles after comminution, it was found that the medium particle size was 1.2 μm. Then 30 parts of glass fibers having an average diameter of 10 μm and a length of 100–300 μm were added to the obtained wet communition production to form a homogeneous slurry (slurry L-1).

Four hundred parts of 4.5 mm-diameter spherical granules of an alumina carrier were introduced into a rotating drum and the slurry L-1 was sprinkled over the carrier while simultaneously heating it by a gas burner from the outside of the drum to evaporate away water. The resulting supported product was subjected to secondary calcination at 500° C. for 2 hours to obtain a supported carrier.

Using the thus obtained supported catalyst, the same reaction process as conducted in Example 1 except for use of tertiary butanol as reaction material was carried out. The results are shown in Table 2.

EXAMPLE 12

(Present Invention)

The procedure of Example 11 was followed except that no glass fiber was used, to obtain a slurry L-2. This slurry was treated in the same way as in Example 11 except that the carrier was used in an amount of 800 parts, to prepare a supported catalyst, followed by the same reaction process as conducted in Example 11. The results are shown in Table 2. Regarding the performance of the obtained supported catalyst, it was slightly inferior to the catalyst obtained in Example 11 in mechanical strength but equal thereto in catalytic activity and selectivity of the objective product.

EXAMPLE 13

(Comparative)

Four hundred parts of a catalytic active substance precursor obtained in the same way as in Example 11 were dry ground using an attritor. Examining the volume-based particle size distribution of the catalytic active substance precursor particles formed by grinding, it was found that the medium particle size was 16.9 μm. Thirty parts of glass fibers having an average diameter of 10 μm and a length of 100–300 μm were added to the dry ground product and the mixture was dispersed in 500 parts of water to form a homogeneous slurry (slurry L-3).

Using this slurry, a supported catalyst was prepared in the same way as in Example 11 and subjected to the same reaction process as in Example 11. The results are shown in Table 2. The performance of the obtained supported catalyst was inferior to that of the catalyst obtained in Example 11 in many respects such as catalytic activity, selectivity of the objective product and mechanical strength.

Industrial Applicability

According to the process of the present invention, it is possible to produce a supported catalyst for the synthesis of methacrolein and methacrylic acid, which is excellent in catalytic activity, selectivity of the objective product and mechanical strength, with ease and good reproducibility.

TABLE 1

| | Composition of catalytic active substance | Primary calcination temperature (°C.) | Medium particle size after comminution (μm) | Amount of supported catalytic active substance per 100 parts by weight of carrier (parts by weight) | Secondary calcination temperature (°C.) | Iso-butylene reaction rate (%) | Selectivity Meth-acrolein (%) | Selectivity Meth-acrylic acid (%) | Rate of powdering after packing (%) |
|---|---|---|---|---|---|---|---|---|---|
| Example 1 | $Mo_{12}Bi_1Fe_2Ni_1Co_7Mg_1Sb_{0.9}$ $Ti_{0.1}Te_{0.02}Cs_{0.4}O_x$ | 300 | 2.1 | 80 | 510 | 96.2 | 88.1 | 5.3 | 0.2 |
| Example 2 | $Mo_{12}Bi_1Fe_2Ni_1Co_7Mg_1Sb_{0.9}$ $Ti_{0.1}Te_{0.02}Cs_{0.4}O_x$ | 300 | 7.2 | 80 | 510 | 96.0 | 88.0 | 5.3 | 0.2 |
| Example 3 | $Mo_{12}Bi_1Fe_2Ni_1Co_7Mg_1Sb_{0.9}$ $Ti_{0.1}Te_{0.02}Cs_{0.4}O_x$ | 230 | 2.1 | 80 | 510 | 96.2 | 88.1 | 5.3 | 0.2 |
| Example 4 | $Mo_{12}Bi_1Fe_2Ni_1Co_7Mg_1Sb_{0.9}$ $Ti_{0.1}Te_{0.02}Cs_{0.4}O_x$ | 360 | 2.1 | 80 | 510 | 96.2 | 88.1 | 5.3 | 0.2 |
| Example 5 | $Mo_{12}Bi_1Fe_2Ni_1Co_7Mg_1Sb_{0.9}$ $Ti_{0.1}Te_{0.02}Cs_{0.4}O_x$ | 300 | 30.3 | 80 | 510 | 93.1 | 86.8 | 4.9 | 0.8 |
| Example 6 | $Mo_{12}Bi_1Fe_2Ni_1Co_7Mg_1Sb_{0.9}$ $Ti_{0.1}Te_{0.02}Cs_{0.4}O_x$ | 450 | 2.1 | 80 | 510 | 92.4 | 85.3 | 4.7 | 0.5 |
| Example 7 | $Mo_{12}Bi_{1.2}Fe_{2.2}Ni_4Co_2Zn_{1.5}$ $Si_1Ce_{0.2}W_{0.5}Rb_{0.2}K_{0.2}O_x$ | 270 | 1.8 | 100 | 495 | 97.5 | 87.8 | 5.1 | 0.2 |
| Example 8 | $Mo_{12}Bi_{1.2}Fe_{2.2}Ni_4Co_2Zn_{1.5}$ $Si_1Ce_{0.2}W_{0.5}Rb_{0.2}K_{0.2}O_x$ | 470 | 1.8 | 100 | 495 | 93.3 | 85.5 | 4.5 | 0.4 |
| Example 9 | $Mo_{12}Bi_{0.9}Fe_{2.5}Co_8Mn_{0.2}$ $Pb_{0.1}P_{0.2}Zr_{0.05}Cs_{0.4}$ $Na_{0.08}O_x$ | 320 | 0.9 | 140 | 520 | 98.7 | 86.0 | 6.0 | 0.2 |
| Example 10 | $Mo_{12}Bi_{0.9}Fe_{2.5}Co_8Mn_{0.2}$ $Pb_{0.1}P_{0.2}Zr_{0.05}Cs_{0.4}$ $Na_{0.08}O_x$ | 520 | 0.9 | 140 | 520 | 91.9 | 85.8 | 5.9 | 1.2 |

TABLE 2

| | Composition of catalytic active substance | Primary calcination temperature (°C.) | Medium particle size after comminution (μm) | Amount of supported catalytic active substance per 100 parts by weight of carrier (parts by weight) | Secondary calcination temperature (°C.) | Tertiary butanol reaction rate (%) | Selectivity Meth-acrolein (%) | Selectivity Meth-acrylic acid (%) | Rate of powdering after packing (%) |
|---|---|---|---|---|---|---|---|---|---|
| Example 11 | $Mo_{12}Bi_1Fe_{2.1}Ni_3Co_3$ $Zn_1Sn_{0.2}B_{0.1}S_{0.01}$ $Ge_{0.09}Tl_{0.1}Cs_{0.4}O_x$ | 300 | 1.2 | 100 | 500 | 100.0 | 87.8 | 5.5 | 0.2 |
| Example 12 | $Mo_{12}Bi_1Fe_{2.1}Ni_3Co_3$ $Zn_1Sn_{0.2}B_{0.1}S_{0.01}$ $Ge_{0.09}Tl_{0.1}Cs_{0.4}O_x$ | 300 | 1.2 | 50 | 500 | 100.0 | 87.8 | 5.5 | 0.3 |
| Example 13 | $Mo_{12}Bi_1Fe_{2.1}Ni_3Co_3$ $Zn_1Sn_{0.2}B_{0.1}S_{0.01}$ $Ge_{0.09}Tl_{0.1}Cs_{0.4}O_x$ | 300 | 16.9 | 100 | 500 | 100.0 | 86.3 | 5.2 | 0.9 |

We claim:

1. A process for producing a supported catalyst for the synthesis of methacrolein and methacrylic acid in which a catalytic active substance comprising a composite oxide containing molybdenum and bismuth as essential components is supported on the inside surface and/or the outside surface of an inert carrier, which comprises drying a mixed solution or an aqueous slurry containing the compounds of the elements constituting said catalytic active substance, subjecting the dry product to a primary calcination at a temperature in a range of 200°–400° C. to form a catalytic active substance precursor, comminuting the obtained catalytic active substance precursor to such an extent that medium particle size in volume-based particle size distribution becomes 10 μm or less, supporting the resulting comminution product on an inert carrier, and subjecting it to a secondary calcination at a temperature which is 100° C. or more higher than the primary calcination temperature.

2. The process according to claim 1, wherein said catalytic active substance precursor is wet comminuted in a state of being dispersed in or wetted with a liquid substance when said catalytic active substance precursor is comminuted.

3. The process according to claims 1 or 2, wherein glass fiber is used as support reinforcement when said comminution product is supported on an inert carrier.

4. The process according to claims 1 or 2, wherein said catalytic active substance comprises a composite oxide represented by the following formula:

wherein Mo, Bi, Fe and O represent molybdenum, bismuth, iron and oxygen, respectively; A represents nickel and/or cobalt; X represents at least one element selected from the group consisting of magnesium, zinc, manganese, tin and lead; Y represents at least one element selected from the group consisting of phosphorus, boron, sulfur, tellurium, silicon, germanium, cerium, niobium, titanium, zirconium, tungsten and antimony; Z represents at least one element selected from the group consisting of potassium, sodium, rubidium, cesium and thallium; and a, b, c, d, e, f, g and h represent the ratios of atoms of the respective elements, wherein when a=12, $0.1 \leq b \leq 5$, $0.1 \leq c \leq 5$, $1 \leq d \leq 12$, $0 \leq e \leq 10$, $0 \leq f \leq 10$, and $0.01 \leq g \leq 3$, and h is the number of the oxygen atoms necessary for satisfying the valences of the respective elements.

* * * * *